United States Patent [19]

Danrée

[11] Patent Number: 4,678,810
[45] Date of Patent: Jul. 7, 1987

[54] MEDICAL USES OF HALOGENOBENZOHENONE-OXIME DERIVATIVES

[75] Inventor: Bernard Danrée, Poissy, France

[73] Assignee: Institut De Recherches Chimiques Et Biologiques of Appliques (I.R.C.E.B.A.), Paris, France

[21] Appl. No.: 833,015

[22] Filed: Feb. 26, 1986

Related U.S. Application Data

[63] Continuation-in-part of Ser. No. 662,285, filed as PCT FR 84/00018 on Jan. 27, 1984, published as WO 84/02844 on Aug. 2, 1984, abandoned.

[30] Foreign Application Priority Data

Jan. 27, 1984 [WO] PCT Int'l Appl. ............ PCT/FR84/00018
Jan. 28, 1983 [FR] France .......................... 83 01365

[51] Int. Cl.$^4$ ................................ A61K 31/15
[52] U.S. Cl. .......................................... 514/640
[58] Field of Search .................... 564/266; 514/640

[56] References Cited

U.S. PATENT DOCUMENTS 4,141,995 2/1979 Saunders et al. ................ 514/640

FOREIGN PATENT DOCUMENTS 2518631 4/1976 Fed. Rep. of Germany ...... 564/266

Primary Examiner—James H. Reamer
Assistant Examiner—L. Hendriksen
Attorney, Agent, or Firm—Holman & Stern, Chartered

[57] ABSTRACT

The invention relates to halogenobenzophenone-oxime derivatives of the general formula

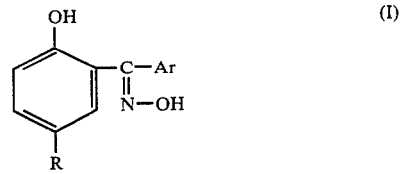

wherein R is $C_3$-$C_8$ alkyl with a branched hydrocarbon chain, and Ar is a halogenophenyl group of the formula

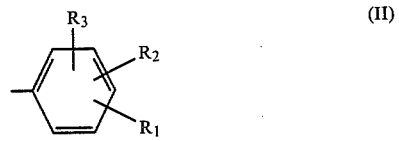

in which $R_1$ is F, Cl or Br, and $R_2$ and $R_3$, identical or different, represent each H, F, Cl or Br.

The derivatives of formula I are useful as antibacterial agents.

3 Claims, No Drawings

MEDICAL USES OF HALOGENOBENZOHENONE-OXIME DERIVATIVES

CROSS REFERENCE TO RELATED APPLICATION(S)

This application is a continuation-in-part application of U.S. patent application Ser. No. 662,285 of Sept. 27, 1984, now abandoned which stemmed from PCT International Application No. PCT/FR 84/00018 filed Jan. 27, 1984.

SCOPE OF THE INVENTION

This invention is concerned with the use of halogenobenzophenone-oxime derivatives as pharmaceuticals and in particular as antibacterial drugs. More precisely it relates to a method of treatment of infectious disease caused by Gram+ bacteriae and some Gram− bacteriae, such as Neisseria, in human beings.

PRIOR ART

It is known that No. DE-A-2 518 631 disclosed some halogenobenzophenone-oxime derivatives as industrial products useful for complexing or chelating metals such as copper. It is also known that U.S. Pat. No. 4,141,995 suggests in its general formula some halogenobenzophenone-oxime derivatives which are lower homologues of the compounds according to the formula I hereinafter (with a group R=H, $CH_3$ or $C_2H_5$ instead of a $C_3$-$C_8$ alkyl group with a branched hydrocarbon chain according to this invention) and exhibit an antiallergy activity.

On the other hand it is known that in the past 2-(halogenobenzyl)-4-alkylphenols (wherein the 4-alkyl group is a branched hydrocarbon radical, in particular an isopropyl, s-butyl, t-butyl or 1,1,3,3-tetramethylbutyl radical) have been proposed as bacterio-static substances in U.S. Pat. Nos. 3,830,852, 3,855,317, 3,984,482 and in BUU-HOI et al., J. Org. Chem., 20, pages 1129-1134 (1955).

It is known that 2-(2,4-dicholrobenzyl)-4-(1,1,3,3-tetramethylbutyl)-phenol (which is coded as "B.11" and which is disclosed in the example 1 of U.S. Pat. No. 3,830,852) has been commercialized in France as an anti-infectious drug (International Common Denomination: "CLOFOCTOL"; trademark of the speciality: "OCTOFENE"). This compound, which is particularly effective in the treatment of infectious diseases caused by Gram+ bacteriae, and its analogues of the 2-(halogenobenzyl)-4-alkylphenol type are not naturally hydrosoluble nor hydrodispersible. The poor affinity for water of said 2-(halogenobenzyl)-4-alkylphenols constitutes a drawback which restricts their use from a galenical point of view.

According to the invention are proposed, as new medicaments, compounds belonging to the family of the halogenobenzophenone-oxime derivatives, which are (i) structurally different from the above mentioned 2-(halogenobenzyl)-4-alkylphenols, on the one hand, and particularly interesting from a therapeutical point of view on account of their affinity for water and of their bacteriostatic and bactericidal properties, on the other hand, (ii) different in view of their structure and activities from their lower homologues of the forementioned U.S. Pat. No. 4,141,995, and (iii) new or already disclosed as complexing agents for metals according to the forementioned No. DE-A-2 518 631.

OBJECT AND DETAILED DISCLOSURE OF THE INVENTION

According to the invention is provided a new method of treatment of infections caused to humans by Gram+ bacteriae and by some Gram− bacteriae such as Neisseria. Said method comprises administering to a patient in need of such a treatment a pharmaceutically antiinfectious effective amount of a compound belonging to the family of halogenobenzophenone-oxime derivatives.

A compound according to the invention which belongs to the halogenobenzophenone-oxime family, is characterised in that it is selected from the group consisting of compounds of the general formula

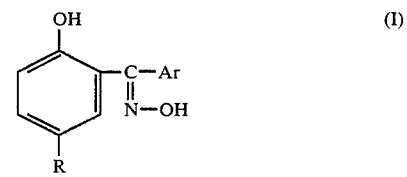

wherein R represents a $C_3$-$C_8$ alkyl group having a branched hydrocarbon chain, and Ar represents a halogenophenyl group of the formula

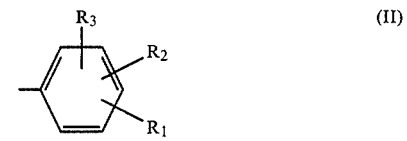

where $R_1$ is F, Cl or Br, and $R_2$ and $R_3$ which may be identical or different represent each H, F, Cl or Br.

Amongst the R alkyl groups, which present a $C_3$-$C_8$ branched hydrocarbon radical and are suitable according to the invention, one can cite the $CH(CH_3)_2$, $C(CH_3)_3$, $CH(CH_3)CH_2CH_3$, $CH_2C(CH_3)_3$, $CH_2CH(CH_3)CH_2CH_3$ and $C(CH_3)_2CH_2C(CH_3)_3$ radicals.

The preferred compounds according to the invention are those wherein R is isopropyl, tert.-butyl, neopentyl or 1,1,3,3,-tetramethylbutyl, and $R_1$ is 4-Cl, $R_2$ is H and $R_3$ is H, 2-Cl or 3-Cl. Said preferred compounds can be represented by the formula

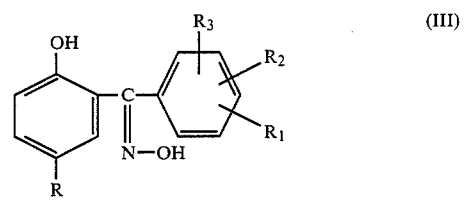

wherein R is $CH(CH_3)_2$, $C(CH_3)_3$, $CH_2C(CH_3)_3$ or $C(CH_3)_2CH_2C(CH_3)_3$, $R_1$ is 4-Cl, $R_2$ is H and $R_3$ is H, 2-Cl or 3-Cl. Amongst those preferred compounds, the most interesting on the therapeutical point of view is 2',4'-dichloro-2-hydroxy-5-(1,1,3,3-tetramethylbutyl)-benzophenone-oxime.

A certain number of compounds which are useful as medicaments according to the invention, are given non-restrictively by way of illustration in table I.

TABLE I

![structure]

Structure: phenol with OH, C(=NOH)-Ar where Ar has R1, R2, R3 substituents; phenol has R substituent.

| Product | R | $R_1$ | $R_2$ | $R_3$ |
|---|---|---|---|---|
| Example 1 | C(CH₃)₂CH₂C(CH₃)₃ | 4-Cl | H | 2-Cl |
| Example 2 | C(CH₃)₂CH₂C(CH₃)₃ | 4-Cl | H | 3-Cl |
| Example 3 | CH₂C(CH₃)₃ | 4-Cl | 3-Cl | 2-Cl |
| Example 4 | CH₂C(CH₃)₃ | 4-Cl | H | H |
| Example 5 | C(CH₃)₃ | 4-Cl | H | 2-Cl |
| Example 6 | C(CH₃)₃ | 4-Cl | H | 3-Cl |
| Example 7 | CH(CH₃)₂ | 4-Cl | 3-Cl | 2-Cl |
| Example 8 | C(CH₃)₃ | 4-F | H | H |
| Example 9 | C(CH₃)₃ | 4-Br | H | 2-Br |
| Example 10 | C(CH₃)₂CH₂C(CH₃)₃ | 4-F | H | 2-Cl |
| Example 11 | CH₂C(CH₃)₃ | 4-Cl | H | 2-Cl |
| Example 12 | C(CH₃)₃ | 4-F | 3-F | 2-F |
| Example 13 | CH₂C(CH₃)₃ | 4-Br | 3-Br | 2-Br |

The halogenobenzophenone-oxime derivatives of formula I can be prepared according to a method known per se by using classical reaction schemes.

The method which is recommended according to the invention for preparing a compound according to formula I consists in reacting a 2-(halogenobenzoyl)-4-alkyl-phenol of the formula

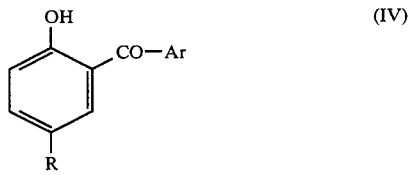

(IV)

(wherein R and Ar are defined as indicated above) with hydroxylamine.

The best mode for carrying out said method comprises reacting a compound of formula IV with hydroxylamine hydrochloride, in pyridine, for at least 10 hours at the reflux temperature of the reaction medium, while using at least 5 mols of hydroxylamine hydrochloride for 1 mol of 2-(halogenobenzoyl)-4-alkylphenol of formula IV.

Formula IV compounds which are used here as starting substances are obtained according to the process disclosed in French patent application No. 83-01364 filed on Jan. 28, 1983.

According to the invention a therapeutical composition is recommended which is characterised in that it comprises, in association with a physiologically acceptable excipient, at least a compound of formula I as active ingredient.

Such a composition, which comprises a pharmaceutically effective amount of active ingredient, can be administered by oral route, rectal route or by injection. Formula I compounds, which exhibit bacteriostatic and bactericidal properties, are more precisely indicated in humans for the treatment of infectious disease caused by Gram+ bacteriae on one hand, and some Gram− bacteriae such as Neisseria on the other hand.

Further advantages and characteristics of the invention will be better understood while reading the following examples of preparation given hereinafter non-restrictively but by way of illustration.

PREPARATION I

Obtention of 2',4'-dichloro-2-hydroxy-5-(1,1,3,3-tetramethylbutyl)-benzophenone-oxime (Example 1; Code No: B.602)

In a three-necked flask fitted with an ascending refrigerating device, a thermometer, a stirring device and an introduction device, 37.93 g (0.1 mol) of 2-(2,4-dichlorobenzoyl)-4-(1,1,3,3-tetramethylbutyl)-phenol and 180 ml of pyridine were introduced under stirring. Then 52.54 g (0.756 mol) of hydroxylamine hydrochloride were introduced while maintaining stirring (the reaction is exothermic at the beginning). The reaction medium was brought to the refluxing temperature for 20 hours. Pyridine was eliminated by evaporation under reduced pressure at 90° C., and the evaporation residue thus obtained was taken up with 200 ml of water. The organical phase was extracted by 3×150 ml of diethylether. The combined ethereal phases were washed with 2×250 ml of HCl 1N then with water up to neutrality, then dried on Na₂SO₄. By concentration under vacuum were obtained 38.6 g (yield: 98%) of a yellowish liquid crystallising by cooling and presenting by thin layer chromatography [plate of silica; eluent: toluene-ethylacetate (95:5) v/v] two stains.

By recrystallisation from hexane were obtained 31.9 g (yield: 81%) of 2',4'-dichloro-2-hydroxy-5-(1,1,3,3-tetramethylbutyl)-benzophenone-oxime exhibiting only one stain by thin layer chromatography. MP$_{inst.}$=146° C.

PREPARATION II

Obtention of 2',4'-dichloro-2-hydroxy-5-tert.-butylbenzophenone-oxime (Example 5)

By using the method given in Preparation I, but by replacing the 2-(2,4-dichlorobenzoyl)-4-(1,1,3,3-tetramethylbutyl)-phenol by the 2-(2,4-dichlorobenzoyl)-4-tert.-butylphenol, the 2',4'-dichloro-2-hydroxy-5-tert.-butyl-benzophenone-oxime was obtained.

The results of the assays carried out with the compound of example 1 (B.602), which is the preferred product according to the invention, and with clofoctol (B.11) as reference product are summed up hereinafter.

A. TOXICITY AND TOLERANCE

Assays were performed on batches of mice (males and females) weighing each from 18 to 20 g and receiving the compounds to be tested at the doses of 0.5 g/kg, 0.8 g/kg, 1 g/kg, 2 g/kg, 3 g/kg and 4 g/kg per os in an aqueous medium containing 20 g/l of carboxymethylcellulose, the animals being observed during the 14 days following administration.

It was observed that (1) on mice, per os, B.602 (DL-50>4 g/kg) is less toxic than B.11 (DL-50=2 g/kg);

(2) B.602 is better tolerated than B.11, particularly in view of certain side effects:

no diarrhoea at the dose of 4 g/kg for B.602 while B.11 begins to induce diarrhoea at the dose of 0.8 g/kg;

no modification of rectal temperature with B.602 at 2 g/kg and 4 g/kg while B.11 reduces the rectal temperature for 48 hours from the dose of 2 g/kg;

no modification of weight with B.602 at 2 g/kg while B.11 induces a slight liver hypertrophy from the dose of 0.8 g/kg.

B. ANTIBACTERIAL ACTIVITY

The antibacterial activity was studied in vitro according to the usual classical dilution techinque with respect to several strains, in order to determine the minimal inhibiting concentration (M.I.C.) i.e. the minimal bacteriostatic concentration.

The results thus obtained are tabulated in table II hereinafter, the strains used being those of the catalogues of the "Institut Pasteur" of Paris, France (abbreviation: CIP), the "Centre International de Distribution de Souches et d'Information sur les Types Microbiens de Lausanne" (abbreviation: La) and the "American Type Culture Collection" (abbreviation: ATCC).

It comes from the assays which were carried out that B.602 according to the invention is particularly interesting against Gram+ strains and is more active than B.11. Moreover B.602 is also active against some Gram− strains such as Neisseria.

TABLE II

| ANTIBACTERIAL ACTIVITY (MIC in μg/ml) | | |
|---|---|---|
| BACTERIAL STRAINS | Example 1 (B.602) MIC | Clofoctol (B.11) MIC |
| *Staphylococcus aureus* London CIP A.238 | 1 | 3 |
| *Staphylococcus aureus* La 634 | 3 | 6 |
| *Staphylococcus aureus* La 636 | 4 | 5 |
| *Staphylococcus aureus* La 659 | 5 | 6 |
| *Staphylococcus aureus* ATCC 6538 P | 4 | 8 |
| *Streptococcus pyogenes* CIP. A 241 | 2 | 4 |
| *Streptococcus pyogenes* CIP. 56.1 | 2 | 3 |
| *Streptococcus pyogenes* CIP. 56.41 | 3 | 4 |
| *Streptococcus pyogenes* CIP. 56.43 | 1 | 2 |
| *Streptococcus pyogenes* CIP. 56.45 | 1 | 2 |
| Streptococcus La 147 | 2 | 7 |
| *Streptococcus faecalis* CIP 53.152 | 3 | 6 |
| *Streptococcus faecalis* CIP 55.142 | 2 | 5 |
| *Diplococcus pneumoniae* La 209 | 4 | 4 |
| *Diplococcus pneumoniae* La 210 | 3 | 5 |
| *Bacillus subtilis* ATCC 6633 | 1 | 4 |

C. CLINICAL ASSAYS

Clinical assays carried out on human beings suffering from infectious disease caused by Gram+ bacteriae and Neisseria Gram− bacteria gave fair and good results, especially when the pharmaceutical composition according to the invention which was administered suitably contained from 0.1 to 95% by weight of at least one compound of the formula I.

For oral administration, the composition is preferably formulated as tablets or gelatine-coated capsules, each tablet or capsule containing from 10 to 200 mg of the active ingredient. For the treatment of infections due to Gram+ bacteriae and Neisseria, such tablets or capsules are suitably administered to human patients at the rate of 2 to 8 tablets or capsules per day, for at least 4 days and preferably from 4 to 7 days, in particular for compound B.602.

Any suitable carrier or excipient may be used in such tablets for oral administration such, for example, as starch, lactose, gum tragacanth, methylcellulose or magnesium stearate (lubricant agent) or if desired sweetening agents.

The compound of Example 1 (B.602) was found in clinical assays very interesting as a bactericidal agent in the treatment of infectious diseases such as acute infections of the otorhinolaryngological system and bronchopathies.

It should be understood that while tablets and capsules are the preferred types of formulations of the composition according to the invention, it is also possible to use formulations of other kinds, such as syrups, suppository and soft capsules.

What is claimed is:

1. A method of treating infectious disease caused by Gram+ bacteria and Neisseria Gram− bacteria comprising administering to a patient in need of such a treatment a pharmaceutically effective amount of a compound of the formula.

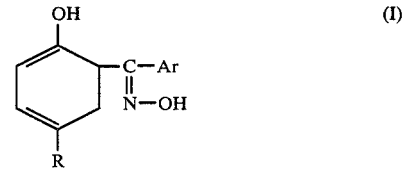

wherein R is a $C_3$–$C_8$ alkyl group with a branched hydrocarbon chain and Ar represents a halogenophenyl group of the formula

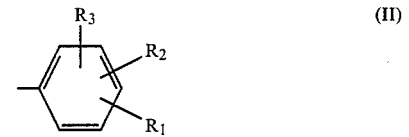

wherein $R_1$ is F, Cl or Br, and $R_2$ and $R_3$, which may be identical or different, represent each H, F, Cl or Br.

2. The method according to claim 1 wherein said compound has the formula

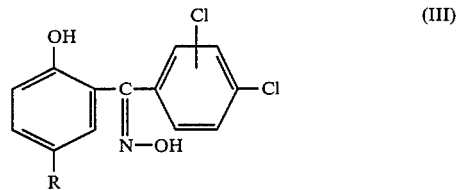

wherein R is $CH(CH_3)_2$, $C(CH_3)_3$, $CH_2C(CH_3)_3$ or $C(CH_3)_2CH_2C(CH_3)_3$.

3. The method according to claim 1 wherein said compound is 2',4'-dichloro-2-hydroxy-5-(1,1,3,3-tetramethylbutyl)-benzophenone-oxime.

* * * * *